United States Patent [19]
Calzi et al.

[11] Patent Number: 4,777,141
[45] Date of Patent: Oct. 11, 1988

[54] INSTRUMENT FOR MEASURING COAGULATION PARAMETERS AND METHOD OF USE

[75] Inventors: Claudio Calzi; Luigi Preda, both of Milano, Italy

[73] Assignee: Fisher Scientific Company, Pittsburgh, Pa.

[21] Appl. No.: 799,675

[22] Filed: Nov. 19, 1985

[30] Foreign Application Priority Data

Nov. 27, 1984 [IT] Italy ................. 23751 A/84

[51] Int. Cl.$^4$ .................. G01N 21/07; G01N 21/47
[52] U.S. Cl. ........................... 436/69; 436/45; 436/165; 436/177; 436/909; 422/72; 422/73
[58] Field of Search ............. 422/72, 73; 436/177, 436/165, 69, 45, 909

[56] References Cited

U.S. PATENT DOCUMENTS

| | | | |
|---|---|---|---|
| 4,226,531 | 10/1980 | Tiffany et al. | 422/258 X |
| 4,252,536 | 2/1981 | Kishimoto et al. | 436/69 X |
| 4,373,812 | 2/1983 | Stein et al. | 422/72 X |
| 4,387,992 | 6/1983 | Swartz | 422/72 X |
| 4,558,946 | 12/1985 | Galle et al. | 422/73 X |

OTHER PUBLICATIONS

C. D. Bertram et al, (Sep. 1984), "Optical Endpoint Sensing in an Automatic Whole Blood Clotting Timer", Med. & Biol. Eng. & Comput., vol. 22, pp. 401–405.

*Primary Examiner*—Michael S. Marcus
*Assistant Examiner*—Lynn M. Kummert
*Attorney, Agent, or Firm*—Alan M. Doernberg

[57] ABSTRACT

An instrument for measuring coagulation parameters is provided in which plasma and at least one reagent are mixed by spinning in a cuvette with transparent windows and in which measurement is then made of scatter by the mixture of the energy of a light beam sent into the mixture.

Upon spin, the plasma components and reagent are displaced into the chamber, thus determining the initiation of the presence of the mixture in which the clot forms, and a photodetecting unit senses the change in the energy of the scattered light, caused by clot formation.

14 Claims, 2 Drawing Sheets

INSTRUMENT FOR MEASURING COAGULATION PARAMETERS AND METHOD OF USE

One of the data significant in the analysis of blood is its predisposition to coagulate: the purpose of coagulation assays is to verify the equilibrium integrity of the hemostasis system.

Measurement of a parameter meaningful for this verification is beset by numerous problems due to a plurality of concomitant circumstances: accuracy and reproducibility of measurement are necessary if the information is to be held truly indicative of the predisposition of a sample to clot and to the extent of the deviation of the measured parameters from standard values in the region of which normal coagulation parameters of a healthy individual can be held to fall.

It is known that in order to measure coagulation time one or more reagents must be mixed with the plasma. The measurement of coagulation time commences from the moment in which the mixing takes place.

Measuring instruments have been proposed which are sensitive to the changes in the physical characteristics of the plasma caused by clot formation.

Some known instruments exploit the principle of mixing the plasma-reagent entity by mechanical agitation means and monitoring the mechanical reaction on said means caused by the sudden localized increase in viscosity in the region of the clot formation. Said instruments are mechanically complicated and provided only approximate measurements, since the presence of an immersed agitator in itself alters coagulation time.

Other known instruments employ a conductimetric measurement between electrodes immersed in the plasma-reagent mixture, exploiting the brusque change in resistance between the electrodes resulting from clot formation between them. However, this method is uncertain and poorly reproducible, and also calls for a complicated cleaning operation with respect to all plasma contacting parts after each measurement.

The known art also suggests a method based on the change in plasma absorbance caused by clot formation. This is a photometric method and provides for the formation of the plasma-reagent mixture in a measuring cuvette which is placed into a photo-optical measurement passageway which measures the absorbance by the plasma of a light beam taken as a sample traverses the cuvette. The chief disadvantage of the instruments using said measurement principles is uncertainty as to the exact localization of the clot being formed with respect to the light beam.

Another generic disadvantage of the known instruments is the non-reproducibility of the activation times (when required) of the different samples to be analyzed.

A further drawback occurring with all the known measuring instruments is the difficulty of mixing the reagent into the plasma without appreciably and irregularly altering the clot formation process; this clearly causes variation of the measured coagulation time.

One object of the present invention is to provide an instrument and method of use for measuring coagulation time of a plasma sample, as an absolute value or a percentage value and/or ratio with respect to standard values, that obviates the disadvantages existing in the prior art and, especially, that allows highly reproducible measurements to be obtained so that the resulting datum will be of particular significance in comparison with a reference value.

Another object of the present invention is that the method should enable the measurement to be done in a rapid and wholly automated manner, especially regarding the mixing of the plasma and coagulation reagent/s, so as to make the measurement independent of a subjective mode of manipulating the mixture variable from sample to sample, which would affect standardization of the measurement and thus its reliability.

A third object of the invention is to permit measurements to be effected in times which are overall very short, so that it can also be employed in extemporaneous emergency analyses.

To such ends, the invention embodies a method of measuring the predisposition of a plasma sample to coagulate and provide for the placement of the plasma and at least one reagent into two chambers, separated by a partial dam, of a cuvette supported by its radial axis in a rotor and featuring at least two substantially orthogonal transparent windows at its base; for the spin-transfer of the component contained in the chamber of the annular radial distance into the adjacent chamber flowing over the dam, in order to mix the components; for directing a light-beam towards the resulting mixture through one of said windows; for measuring the light scattered by said mixture by photodetection of the light emerging from the other of said windows; for comparing the intensity of the mixture light-scatter with that of a reference substance light-scatter; for determining the variation with time of the comparative value thus obtained.

Specifically, the method according to the invention provides for the use of a reference substance consisting of an emulsion; an emulsion of silicone oil in water has been found to be advantageous.

The reference substance simulates a light-scatter signal comparable to that of a normal clot, in which normality is referred to by the size and density of the clot and thus to its ability to reflect light.

According to the present method the coagulation curve, which represents the progression of clot formation over time, is measured for each sample to be analyzed; the values represented by said curve are processed by means of appropriate algorithms and the coagulation time and other correlated parameters are in this way determined for all coagulimetric tests. Fibrinogen content can also be determined.

As compared to the known methods, the method according to the invention provides data of surprising reproducibility.

The greater precision of the measurement obtained by the method according to the invention compared generally to the methods employing absorbance measurements is due to the fact that the progression of clot formation is better described by measuring clot light-scatter than by measuring clot light-absorbance.

This is because, as will become more apparent hereinafter, the final coagulation stage, i.e. the conversion of fibrinogen to fibrin, changes the system from a liquid to a solid state.

The initial homogeneous liquid phase gives way to a heterogeneous light-solid phase in which the first threads of insoluble fibrin are formed (these being the primary light-scatter centres), on which, by an understood process of thread-enmeshment of blood cells and squeezing out the serum, the clot is formed.

The final phase is a homogeneously solid one in which all the fibrinogen has been converted into insoluble fibrin.

The objects and advantages of the invention and its practical application will become more apparent from the following illustrative description of one form or embodiment thereof, with reference to the appended drawings in which.

Figure 1:
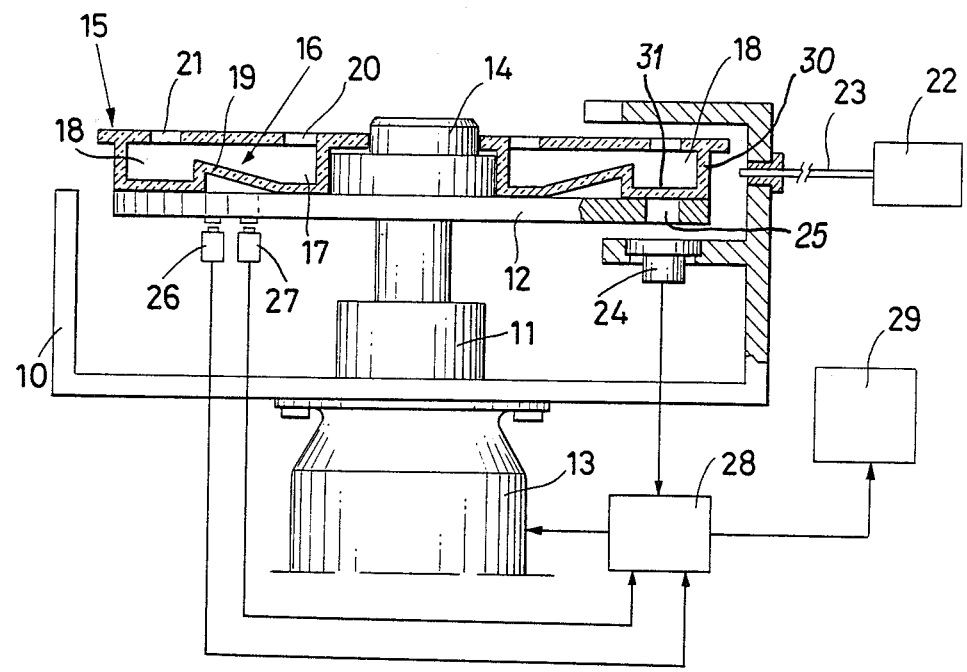
FIG. 1 is a partial schematic of the significant part of an instrument for effecting the measurement.

As FIG. 1 shows, the instrument for effecting the measurement according to the invention comprises a structure 10 in which there is rotatably supported at 11 a disc 12 rotated by a motor partially shown at 13. The disc 12 carries a hub 14 to which is removably restrained a sample-holder rotor 15 in which are formed radial elongated hollow shaped cuvettes indicated overall by 16.

Each cuvette is divided into chambers 17 and 18 by a ramp-shaped dam 19, and each chamber communicates externally by means of passages 20 and 21.

The sample-holder rotor 15 is fabricated of transparent plastic material. As it is per se known, e.g. from the specification of the Italian application No. 20 560 A/83 of Instrumentation Laboratory S.P.A., the general structure of the instrument and its sample-holder plate is here described only summarily.

The invention provides for a light source 22 which sends a light beam, through for example a bundle of optical fibers 23, to the outermost wall of the cuvettes 16. A photodetecting unit 24 is provided in a position orthogonal to the light beam, and is reached by the light scattered by the material contained in chamber 18, through a bore 25 in the disc 12 on which rotor 15 is supported.

The instrument comprises detectors 26 and 27 which detect the velocity and position of the rotor 15 and which send corresponding signals to a processing unit 28, to which the signal of the photodetecting unit 24 is also sent. The processor 28 produces a signal which operates the motor 13 and also a signal which is a function of the signal of the photodetecting unit 24; this latter signal is sent to a data display unit 29.

The light source 22 can be of various kinds, in particular a He-Ne laser which is advantageous as a result of the intensity and acceptable constancy of its monochromatic light energy, characterized by a relatively long useful life. This type of laser has also been found opportune as a light source by reason of the wavelength of the radiation emitted, the experimental sensitivity of the measurement having proved maximal with radiation in the red region of the spectrum.

Figure 3:
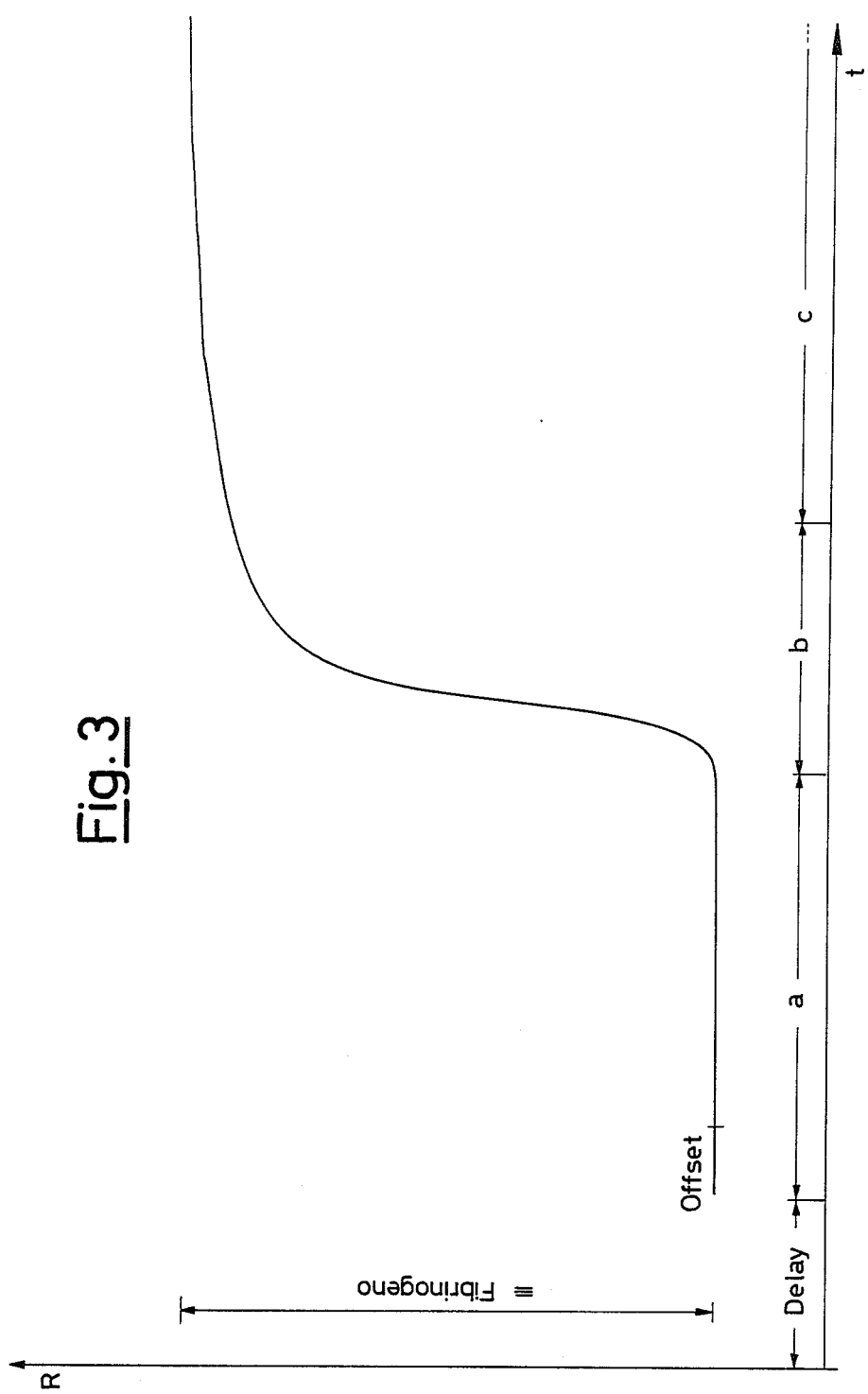
FIG. 3 is a diagram of the signal detected by the instrument as a function of clot formation.

The operating mode of the method and instrument according to the invention will become more apparent from FIG. 3, which shows a typical clot formation curve, valid for all coagulation analyses.

FIG. 3 shows time on the abscissa and the parameter R represents the ratio between the light scattered by the test sample and the light scattered by the optical reference substance (emulsion).

If the instrument measures light-scatter every rotor revolution, exemplified as 1200 rpm, the curve is plotted with a measurement every 50 milliseconds. The time between measurements can, however, be selected as a function of the precision required of the measurement.

The light-scatter of the optical reference substance is measured at time intervals sufficiently small to allow the light emitted by the source to be considered constant for the purpose of the sensitivity foreseen for the measurement.

The resulting curve consequently represents only the clot formation process, eliminating any influence due to possible instability of the light source.

Figure 2:
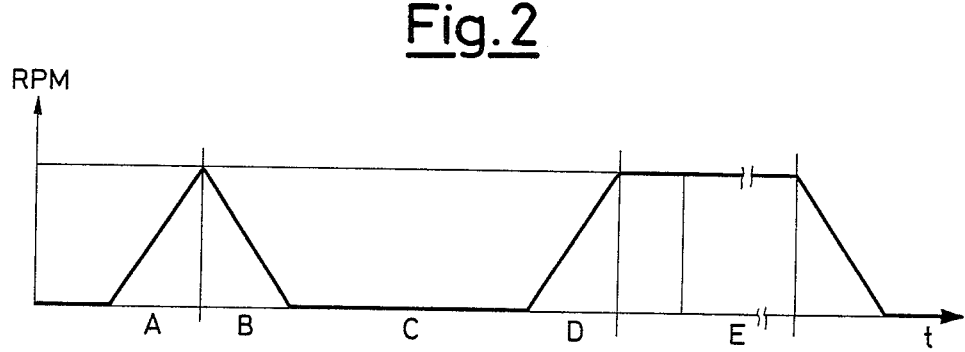
FIG. 2 is an operational schematic for the instrument.

When the mixing cycle as shown in FIG. 2 is complete, provision is made for a delay, which varies depending on the reaction it is wished to monitor.

By measuring the initial points of the curve, measured for instance in the first second of time, the instrument determines a base value of light scatter peculiar to each sample and subtracts such value from subsequent measured values to zero the curve and render the starting point equal for all the curves.

The differences in turbidity between pathological and normal plasma or the different opacity of the reagents will therefore have no effect on measurement or comparison between measurements.

The curve of FIG. 3 can be subdivided into three parts, each of which represents a particular phase of the clot formation process:

(a) liquid sample-reagent mixture without fibrin;
(b) initiation of insoluble fibrin formation with rapid conversion of fibrinogen;
(c) stabilization of the fibrin clot.

The final light-scatter value (after subtracting base value of light scatter) is a function of a parameter correlated with the amount of clottable fibrinogen present in the sample. The operating mode of the instrument illustrated is described below with respect to two typical cycles, and more exactly:

cycles in which one reagent is added to the plasma, the PT cycle being an example of these;

cycles in which two reagents are added to the plasma separately and in succession, the APTT cycle being an example of these.

Execution according to the present invention of the PT cycle is as follows: a plasma sample and the reagent (typically calcium thromboplastin (Factor IV)) are simultaneously introduced into the pair of passages 21 and 20 so as to occupy the chambers 17 and 18 of a, respectively.

When the cuvettes 16 have been loaded in the manner described, one of them however containing the optical reference emulsion, the rotor is spun so that the plasma is obliged by centrifugal force to overflow the ramp-shaped dam 19 and to reach the chamber 18 where it mixes with the reagent.

Complete mixing of the components is caused by rapid acceleration of the sample-holder rotor followed by a rapid deceleration ending in arrest (to optimize the mixing of plasma and reagent) and the rotor remains arrested for a few seconds; the rotor is then re-accelerated up to about 1200 rpm and data acquisition then begins; this clearly lasts for a period greater than the longest time expected to be measured for coagulation, for example about one minute.

The schematic of FIG. 2 shows a typical movement cycle of the rotor 15 in which the times are reported on the abscissa and on the ordinate the angular velocities of the controlled rotor of the processing unit 28, to which the signal of the photodetecting unit 24 is also delivered.

The time intervals A, B and D are, each, for example, 0.4 seconds; the time interval C is approximately 3 seconds. The measurement is made singly for each cuvette through a discrimination of the rotor position detected by detector 27. For each cuvette, therefore, the light-scatter displayed by detector device 29 is measured by detector 24; an illustrative time course of light intensity is illustrated in the schematic of FIG. 3.

The time value which it is wished to obtain with the PT assays is thus obtainable by defining in a pre-determined manner the point on the curve at which the process of clot formation is conventionally held to initiate: said point can be pre-selected as the inflexion point of the curve in the area (b) or as being the point at which the value of R deviates to a pre-set extent from the initial value (base value) of the curve, or according to some other criterion chosen in advance by the investigator which can per se be arbitrary, since it is to the reproducibility of the coagulation curve that importance attaches.

It should be noted that, as mentioned previously, the curve of FIG. 3 provides spontaneous information regarding the fibrinogen contained in the plasma sample, i.e. without supplemental operations being required.

For the difference between the initial R value and the value tending to an asymptotic constancy corresponding to the effective end of coagulation is an index correlated with the percent content of active fibrinogen that can be converted to fibrin.

This important analytical datum can therefore also be obtained by the analysis performed with the method and instrument according to the invention.

A 2-reagent cycle is described below in respect of the typical case of the APTT cycle.

A plasma sample and the first reagent (typically cephalin+ellagic acid) are simultaneously placed into the pair of passages 20 and 21 so as to occupy the chambers 17 and 18 respectively.

When the cuvettes 16 of the rotor have been loaded as described, the rotor 15 is spun so that the plasma is forced to overflow the ramp-shaded dam 19 and to reach the chamber 18 where it mixes with the reagent.

Complete mixing of the components is caused by rapid acceleration of the sample-holder rotor 15 followed by a rapid deceleration ending in arrest, which is maintained for a few seconds in order to improve the mixing of the plasma with the first reagent; the rotor 15 is then re-accelerated up to about 1200 rpm and remains at said velocity for 60 seconds. This time period, known as drying time, enables the plasma to be totally transferred from chamber 17 to chamber 18 and also permits drying of the chamber 17, which will receive the second reagent (typically CaCl).

By "drying" is here meant the removal of the very fine surface film of liquid that can cause migration, through capillarity, from chamber 17 to chamber 18. Loading of the second reagent into the passage 20 is then commenced so that it will occupy the chamber 17.

When the cuvettes 16 of the rotor 15 have been loaded as described, three hundred seconds after the first mixing the rotor 15 is spun so as to cause the second reagent to overflow the ramp-shaped dam 19 and reach the chamber 18, where it mixes with the plasma already mixed with the first reagent.

Complete mixing of the components is produced by rapid acceleration of the sample-holder rotor 15 followed by rapid deceleration ending in arrest, which is maintained for a few seconds to improve the mixing of the plasma/first reagent mixture with the second reagent. The rotor 15 is then re-accelerated up to about 1200 rpm and data acquisition then starts and, as will be clear, lasts for a period greater than the longest time expected to be measured for coagulation, for example 70 seconds.

Measurement is individual for each cuvette, through a discrimination of rotor position effected by detector 27.

In consequence, the light-scatter value displayed by display device 29 for each cuvette is measured by detector 24, thus providing a light intensity time course curve, again of the type shown in FIG. 3.

The processing unit 28 therefore processes as a function of time, and in a manner per se known, the signals operating the rotation of the motor 13, as also the synchronizing signals as a function of time and rotor position, which synchronizing signals deliver the signals relating to the light-scatter measured by detector 24 to the data display unit 29.

In modes per se known, the processing unit 28 also controls the egress of light-scatter signals from the cuvette containing reference emulsion in pre-set time intervals, and performs the calculations required to obtain the significant analytical data by processing the data measured for the plotting as previously described of the curve of FIG. 3, for analysis of the course of said curve and for determination of the characteristic points on said curve, however these may be defined.

The above described embodiment of the instrument and its method of use illustrate the principles of the present invention and are not limiting.

Numerous variants and modifications can be made thereto without exceeding the scope of the invention.

More specifically, the optical means used to send the light beam to the base of the cuvette can be different from the means herein described, as also the means employed to received the light-scatter in an orthogonal direction, to send it to a transducer that can provide a signal which is a function of the intensity of said light-scatter.

The light source herein described as being advantageously a He-Ne laser may also be different, although a source of monochromatic light or in any case narrow-band light, in particular in the red region of the spectrum, benefits precision of measurement.

No description has been given above of the instrumental accessories such as the devices for placing the plasma sample and reagent into the cuvettes, since these are either per se known or not strictly necessary for enacting the invention; said devices can consist advantageously of an arm carrying two terminal needles of ducts which are in a sequential manner brought proximal to take-off vessels and proximal to the bores communicating with the chambers of the cuvettes, for complete automation of the measuring operation.

We claim:

1. A method for measuring the predisposition of a plasma sample to clot comprising the steps:
   (a) providing a rotor with multiple radially-extending cuvettes, each cuvette having an inner chamber and an outer chamber separated by a partial dam and having a radially-exterior basewall; the outer chamber being provided with two orthogonal windows, one of which is located on the exterior basewall of the rotor;
   (b) placing a plasma sample into one of the chambers of a cuvette,
   (c) placing a coagulation reagent into the other chamber of the same cuvette,
   (d) transferring the material in the inner chamber over the partial dam to the outer chamber to mix the components and initiate a coagulation reaction, (e) directing a light beam into the outer chamber through one of the orthogonal windows, (f) detecting light emerging from the other of the orthogonal windows over a plurality of points of time as a measure of the light scattered by the mixture of components at each point of time, (g) measuring the light scattered by passing the light beam through a reference substance at each point of time, (h) comparing at each point of time the light scattered by the mixture of components and by the reference substance to determine at each point of time a comparative value of light scatter, and (i) determining from the plurality of comparative values of light scatter a clotting time for the plasma sample.

2. The method of claim 1 wherein the plasma sample is placed in the outer chamber of a cuvette.

3. The method of claim 1 wherein the light beam is monochromatic and in the red region of the spectrum.

4. The method of claim 1 wherein the determining step (i) further comprises determining from the change in comparative light scatter between an initial point of time and a final point of time the amount of fibrin formed by reaction between the plasma sample and the coagulation reagent.

5. The method of claim 1 wherein multiple plasma samples are each placed in the outer chamber of cuvettes in the same rotor.

6. The method of claim 5 wherein the reference substance is an emulsion present in the outer chamber of a cuvette into which plasma sample and coagulation reagent are not placed.

7. The method of claim 5 wherein an identical coagulation reagent is placed into the inner chamber of each cuvette into whose outer chamber a plasma sample is placed.

8. The method of claim 7 wherein the transferring step (d) comparing step (h) and determining step (i) are performed concurrently for each cuvette.

9. The method of claim 7 wherein the light beam in monochromatic and in the red region of the spectrum.

10. A method for measuring the predisposition of a plasma sample to clot comprising the steps:
(a) providing a rotor with multiple radially-extending cuvettes, each cuvette having an inner chamber and an outer chamber separated by a partial dam and having a radially-exterior basewall; the outer chamber being provided with two orthogonal windows, one of which is located on the exterior basewall of the rotor;
(b) placing a plasma sample into one of the chambers of a cuvette,
(c) placing a coagulation reagent into the other chamber of the same cuvette,
(d) transferring the material in the inner chamber over the partial dam to the outer chamber to mix the components and initiate a coagulation reaction,
(e) directing a light beam into the outer chamber through one of the orthogonal windows,
(f) detecting light emerging from the other of the orthogonal windows over a plurality of points of time as a measure of the light scattered by the mixture of components at each point of time,
(g) measuring the light scattered by passing the light beam through a reference substance which is a stable emulsion at each point of time,
(h) comparing at each point of time the light scattered by the mixture of components and by the reference substance to determine at each point of time a comparative value of light scatter, and
(i) determining from the plurality of comparative values of light scatter a clotting time for the plasma sample.

11. A method according to claim 10, characterized in that said emulsion is an emulsion of silicone oil in water.

12. A method for measuring the predisposition of a plasma sample to clot comprising the steps:
(a) providing a rotor with multiple radially-extending cuvettes, each cuvette having an inner chamber and an outer chamber separated by a partial dam and having a radially-exterior basewall; the outer chamber being provided with two orthogonal windows, one of which is located on the exterior basewall of the rotor,
(b) placing multiple plasma samples each into the outer chamber of a cuvette,
(c1) placing an identical coagulation activating reagent into the inner chamber of each cuvette into which a plasma sample is placed,
(d1) transferring the coagulation activating reagent in the inner chamber over the partial dam to the outer chamber to mix the components in multiple outer chambers,
(c2) placing an identical coagulation initiating reagent into the inner chamber of each cuvette in which components have been mixed in the outer chamber,
(d2) transferring the coagulation initiating reagent in the inner chamber over the partial dam to initiate a coagulation reaction in multiple outer chambers,
(e) directing a light beam into each outer chamber in which a coagulation reaction is occurring through one of the orthogonal windows,
(f) detecting light emerging from the other of the orthogonal windows over a plurality of points of time as a measure of the light scattered by the mixture of components in an outer chamber in which a coagulation reaction is occurring at each point of time,
(g) measuring the light scattered by passing the light beam through a reference substance at each point of time,
(h) comparing at each point of time the light scattered by the mixture of components in an outer chamber in which a coagulation reaction is occurring and by the reference substance to determine at each point of time a comparative value of light scatter, and
(i) determining from the plurality of comparative values of light scatter a clotting time for each plasma sample.

13. The method of claim 12 wherein a delay occurs between the transferring step (d1) and the transferring step (d2) sufficiently long for the activating reagent to activate each plasma sample for the coagulation reaction subsequently initiated by the coagulation initiating reagent.

14. A method for measuring the predisposition of a plasma sample to clot comprising the steps:
(a) providing a rotor with multiple radially-extending cuvettes, each cuvette having an inner chamber and an outer chamber separated by a partial dam and having a radially-exterior basewall; the outer chamber being provided with two orthogonal windows, one of which is located on the exterior basewall of the rotor, (b) placing multiple plasma samples each into the outer chamber of a cuvette, (c) placing an identical coagulation reagent into the inner chamber of each cuvette into which a plasma sample is placed, (d) transferring the material in the inner chamber over the partial dam to the outer chamber to mix the components and initiate a coagulation reaction in multiple outer chambers by:

(d1) accelerating the rotor to transfer the coagulation reagent over each partial dam into an outer chamber, (d2) decelerating the rotor, and (d3) reaccelerating the rotor to complete the simultaneous mixing of each plasma sample with coagulation reagent, (e) directing a light beam into each outer chamber in which a coagulation reaction is occurring through one of the orthogonal windows, (f) detecting light emerging from the other of the orthogonal windows over a plurality of points of time as a measure of the light scattered by the mixture of components in an outer chamber in which a coagulation reaction is occurring at each point of time, (g) measuring the light scattered by passing the light beam through a reference substance at each point of time, (h) comparing at each point of time the light scattered by the mixture of components in an outer chamber in which a coagulation reaction is occurring and by the reference substance to determine at each point of time a comparative value of light scatter, and (i) determining from the plurality of comparative values of light scatter a clotting time for each plasma sample.

* * * * *